(12) United States Patent
Ferris et al.

(10) Patent No.: US 12,419,730 B2
(45) Date of Patent: *Sep. 23, 2025

(54) DENTAL MEDICAMENT APPLICATOR

(71) Applicant: Cav-Aid LLC, Boerne, TX (US)

(72) Inventors: Tyler Ferris, Boerne, TX (US); Jeff Reeh, Boerne, TX (US)

(73) Assignee: Cav-Aid LLC, Boerne, TX (US)

( * ) Notice: Subject to any disclaimer, the term of this patent is extended or adjusted under 35 U.S.C. 154(b) by 411 days.

This patent is subject to a terminal disclaimer.

(21) Appl. No.: 17/929,081

(22) Filed: Sep. 1, 2022

(65) Prior Publication Data

US 2023/0000603 A1    Jan. 5, 2023

Related U.S. Application Data

(63) Continuation-in-part of application No. 17/668,840, filed on Feb. 10, 2022, now Pat. No. 11,439,489.
(Continued)

(51) Int. Cl.
  *A61K 8/21* (2006.01)
  *A61C 19/06* (2006.01)
  *A61Q 11/00* (2006.01)

(52) U.S. Cl.
  CPC .............. *A61C 19/063* (2013.01); *A61K 8/21* (2013.01); *A61Q 11/00* (2013.01); *A61K 2800/87* (2013.01); *A61K 2800/92* (2013.01)

(58) Field of Classification Search
  CPC ....... A61C 19/063; A61C 5/85; A61C 9/0033; A61C 5/82; A61C 5/88; A61K 8/21;
(Continued)

(56) References Cited

U.S. PATENT DOCUMENTS

| | | |
|---|---|---|
| 3,679,360 A | 7/1972 | Rubin et al. |
| 4,226,848 A | 10/1980 | Nagai et al. |
| (Continued) | | |

FOREIGN PATENT DOCUMENTS

| | | |
|---|---|---|
| DE | 202009009789 | 10/2009 |
| EP | 1263347 | 5/2007 |
| (Continued) | | |

OTHER PUBLICATIONS

SmileCare (A subscription-based discount health care plan) [online]. [retrieved Oct. 19, 2023]. Retrieved from the Internet: https://www.smilecareplymouth.co.uk/blog/what-is-the-average-length-of-the-teeth-importance-in-dental-aesthetics/#:~:text=So%20that%3A,and%20in%20women%206.13%20millimeters. (Year: 2023).*

(Continued)

*Primary Examiner* — Eric J Rosen
*Assistant Examiner* — Luis Ruiz Martin
(74) *Attorney, Agent, or Firm* — Scott Griggs; Griggs Bergen LLP

(57) ABSTRACT

A dental medicament applicator is disclosed. In one embodiment, a placement device is sized for insertion at a dental site, such as an interproximal site. The placement device includes a central body and at least one active matrix secured to the central body containing a topical substance, such as a fluoride-containing chemical agent, silver diamine fluoride, or a peptide-based chemical agent, for example. One or two wings extend from the central body to provide subterminal opposition surfaces to hold the placement device during placement. The one or more wings are free of the topical substance. The active matrix, in response to being physically affixed to the dental site, delivers the topical substance at a controlled rate to the dental site while the placement device dissolves at a quicker controlled rate.

24 Claims, 5 Drawing Sheets

Related U.S. Application Data

(60) Provisional application No. 63/147,751, filed on Feb. 10, 2021.

(58) Field of Classification Search
CPC ............ A61K 2800/87; A61K 2800/92; A61K 9/0053; A61Q 11/00
See application file for complete search history.

(56) References Cited

U.S. PATENT DOCUMENTS

| | | | |
|---|---|---|---|
| 4,568,535 | A | 2/1986 | Loesche |
| 4,837,007 | A | 6/1989 | Duckworth et al. |
| 5,049,077 | A | 9/1991 | Goldin |
| 5,087,200 | A | 2/1992 | Brajnovic et al. |
| 5,154,612 | A | 10/1992 | Carlsson et al. |
| 6,287,120 | B1 * | 9/2001 | Wiesel ............ A61K 8/21 433/80 |
| 6,565,960 | B2 | 5/2003 | Koob et al. |
| 6,827,575 | B1 | 12/2004 | Jorneus |
| 7,056,118 | B2 | 6/2006 | Allred et al. |
| 7,118,376 | B2 | 10/2006 | Jodaikin et al. |
| D549,829 | S | 8/2007 | Jodaikin et al. |
| D553,245 | S | 10/2007 | Jodaikin et al. |
| 7,491,058 | B2 | 2/2009 | Jorneus et al. |
| D605,773 | S | 12/2009 | Jodaikin et al. |
| 7,797,912 | B2 | 9/2010 | Hammond et al. |
| 7,850,453 | B2 | 12/2010 | Jodaikin et al. |
| 7,883,336 | B2 | 2/2011 | Hansson |
| 8,287,277 | B2 | 10/2012 | Jodaikin et al. |
| 9,668,844 | B2 | 6/2017 | Jodaikin et al. |
| 10,849,729 | B2 | 12/2020 | Sagel et al. |
| 10,960,192 | B2 | 3/2021 | Masri et al. |
| 11,439,489 | B2 | 9/2022 | Ferris et al. |
| 2005/0048102 | A1 | 3/2005 | Tapolsky et al. |
| 2005/0175959 | A1 * | 8/2005 | Jodaikin ............ A61C 19/063 433/80 |
| 2005/0196727 | A1 | 9/2005 | Jessop |
| 2005/0239015 | A1 | 10/2005 | Dragan |
| 2010/0203467 | A1 | 8/2010 | Karazivan |
| 2011/0200972 | A1 | 8/2011 | Mythen |
| 2014/0186427 | A1 | 7/2014 | Breitenbach et al. |
| 2015/0125810 | A1 * | 5/2015 | Jodaikin ............ A61C 19/063 433/80 |
| 2015/0290122 | A1 | 10/2015 | Boe |
| 2021/0000579 | A1 | 1/2021 | Higdon |
| 2021/0030668 | A1 | 2/2021 | Schmitz et al. |
| 2021/0186672 | A1 * | 6/2021 | Wandera ............ A61C 19/066 |
| 2022/0249217 | A1 | 8/2022 | Ferris et al. |

FOREIGN PATENT DOCUMENTS

| | | |
|---|---|---|
| WO | 1998016503 | 4/1998 |
| WO | 2017182425 | 10/2017 |

OTHER PUBLICATIONS

Hal Open Science (a multi-disciplinary open access archive for the deposit and dissemination of scientific research documents)[ online]. [retrieved Mar. 28, 2024]. Retrieved from the Internet: https://inria.hal.science/hal-02443460/document (Year: 2023).*

Shutz Dental Micerium Group, Impla Interim Implant, Impla temp. implant, 3,3/11,5mm, 10pcs, The Interim Implant, for securely fixing drilling templates and temporary bridges, date accessed Jul. 7, 2011, 1 page, Rosbach, Germany.

WIPO International Search Report and Written Opinion of the International Searching Authority for PCT/US2022/016006 dated May 6, 2022.

Chong et al., "Slow-release fluoride devices for the control of dental decay (Review)." Cochrane Database of Systematic Reviews 2018, Issue 3, Art. No. CD005101 (Year: 2018).

Tommasina Coviello et al., "Polysaccharide hydrogels for modified release formulations (Review)." University "La Sapienza", Faculty of Pharmacy, P.le Aldo Moro 5, 00185 Rome, Italy. ScienceDirect Journal of Controlled Release 119 (2007) 5-24; www.elsevier.com/locate/jconrel.

Ana Filipa Borges et al., "Oral films: current status and future perspectives. Galenical development and quality attributes." Bluepharma, Indústria Farmacêutica, S.A.Faculty of Pharmacy, University of Coimbra CIEPQPF—Faculty of Sciences and Technology, University of Coimbra. © 2019. This manuscript version is made available under the Elsevier user license; http://www.elsevier.com/open-access/userlicense/1.0/.

M A Shadab Siddiqui et al., "Bioinspired composite structures: A comprehensive review of natural materials, fabrication methods, and engineering applications." Department of Mechanical Engineering, Chittagong University of Engineering & Technology, Chattogram 4349, Bangladesh. ScienceDirect Journal homepage: www.sciencedirect.com/journal/composites-part-c-open-access, Composites Part C: Open Access 17 (2025) 100578. https://doi.org/10.1016/j.jcomc.2025.100578.

Jianjun Yan et al., "Preparation and Properties of Pullulan Composite Films." School of Textiles, Tianjin Polytechnic University, Tianjin, 300387, China. Advanced Materials Research vols. 476-478 (2012) pp. 2100-2104, Online available since Feb. 27, 2012 at www.scientific.net, © (2012) Trans Tech Publications, Switzerland, doi: 10.4028/www.scientific.net/AMR.476-478.2100.

Daniela Pasqui et al., "Polysaccharide-Based Hydrogels: The Key Role of Water in Affecting Mechanical Properties." Interuniversity Research Centre for Advanced Medical Systems (C.R.I.S.M.A.), Viale Matteotti 15, Colle di Val d'Elsa Siena 53034, Italy; E-Mails: pasqui3@unisi.it (D.P.); milena.decagna@virgilio.it (M.D.C.). Polymers 2012, 4, 1517-1534; doi:10.3390/polym4031517. Polymers ISSN 2073-4360 www.mdpi.com/journal/polymers. Published: Aug. 21, 2012.

Emma Adriana Ozon et al., "Three-Dimensional Printing Technologies in Oral Films Manufacturing—A Minireview." Faculty of Pharmacy, Department of Pharmaceutical Technology and Biopharmacy, "Carol Davila" University of Medicine and Pharmacy, 020956 Bucharest, Romania; emma.budura@umfcd.ro (E.A.O.); oana.karampelas@umfcd.ro (O.K.). Processes 2023, 11, 2628. https://doi.org/10.3390/pr11092628. Published: Sep. 3, 2023. Copyright: © 2023 by the authors. Licensee MDPI, Basel, Switzerland.

Extended European Search Report (EESR) for EP 23194463.8-1122 dated Jan. 18, 2024.

* cited by examiner

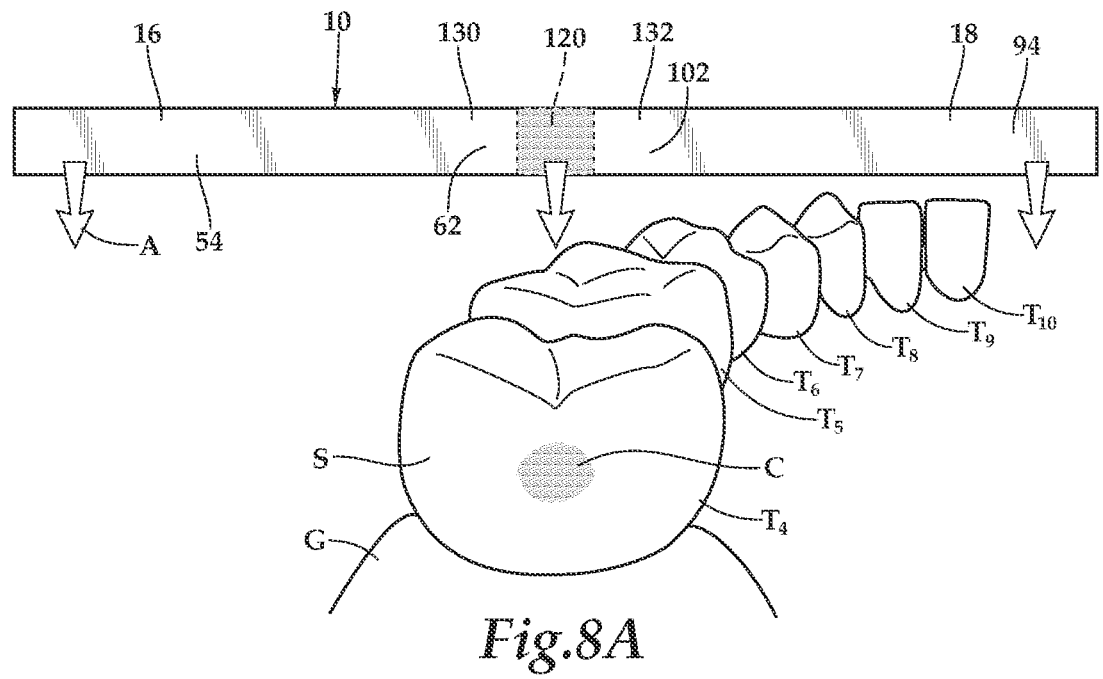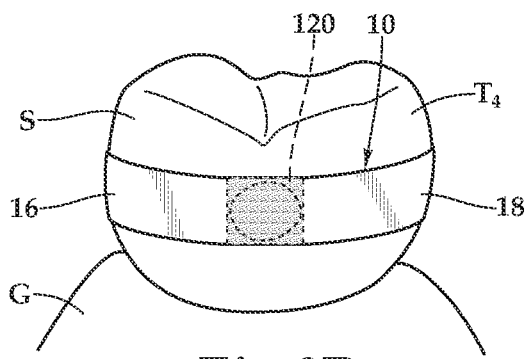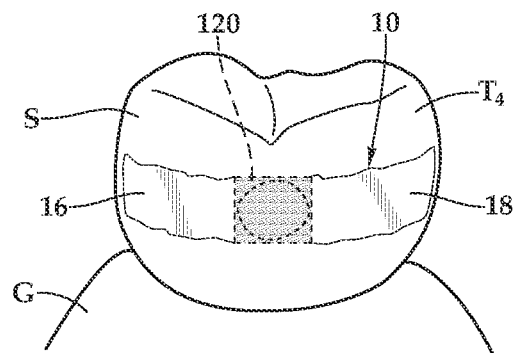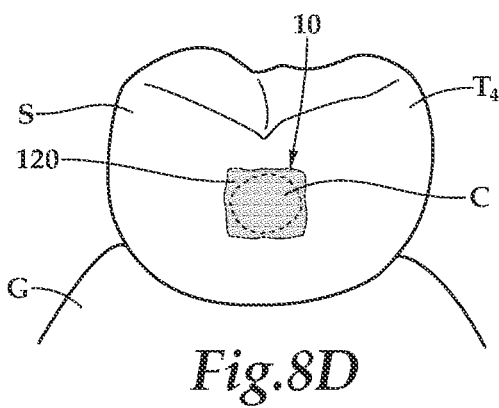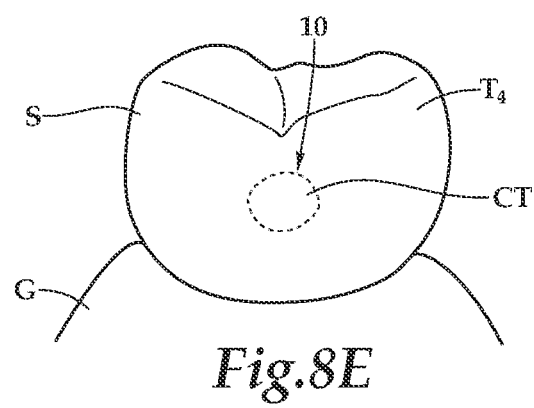

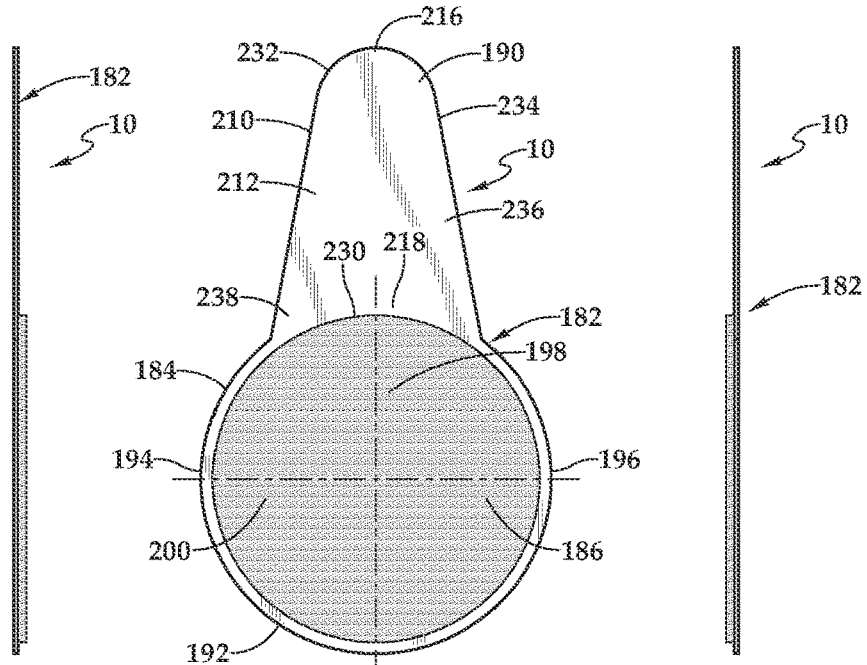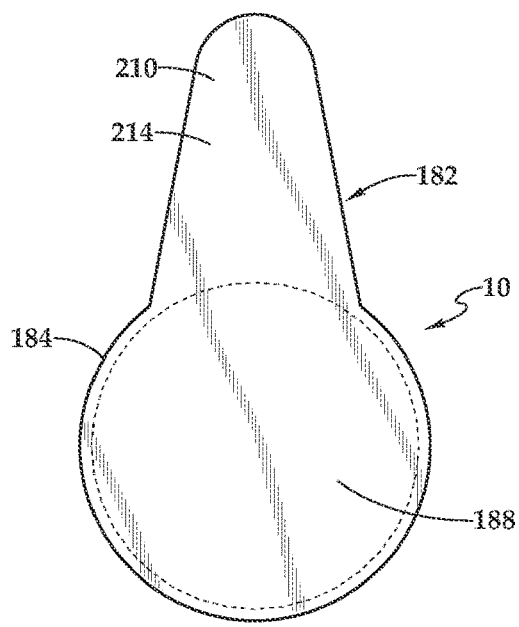

DENTAL MEDICAMENT APPLICATOR

PRIORITY STATEMENT & CROSS-REFERENCE TO RELATED APPLICATIONS

This application is a continuation-in-part of co-pending U.S. patent application Ser. No. 17/668,840, entitled "Dental Medicament Applicator" filed on Feb. 10, 2022, in the names of Tyler Ferris et al., and issued on Sep. 13, 2022 as U.S. Pat. No. 11,439,489; which claims priority from U.S. Patent Application No. 63/147,751, entitled "Dental Medicament Applicator" and filed on Feb. 10, 2021, in the names of Tyler Ferris et al.; both of which are hereby incorporated by reference, in entirety, for all purposes.

TECHNICAL FIELD OF THE INVENTION

The present disclosure relates, in general, to dental devices for treatment and care of the teeth in an oral cavity, and more particularly, to a dental medicament applicator for treating interproximal caries and the like.

BACKGROUND OF THE INVENTION

Dental caries, which are also referred to as tooth decay or cavities, are one of the most common and widespread persistent diseases in the oral cavity. When an individual eats certain food, bacteria in the oral cavity break down the food and produce acids that have the ability to seriously damage hard tissues of a tooth in the oral cavity. The result may be the formation of dental caries. In current clinical dentistry practice, interproximal caries are extremely difficult to treat due to the location of the dental caries between teeth. Accordingly, there is a need for improved systems and methods for effectively treating dental caries and, in particular, hard to reach interproximal caries.

SUMMARY OF THE INVENTION

It would be advantageous to achieve systems and methods that would improve upon existing limitations in functionality with respect to treatment of dental caries and, in particular, interproximal caries. It would also be desirable to enable a mechanical-based and chemical-based medical solution that would provide simplified and accelerated treatment of interproximal caries. It would be further advantageous to enable a form factor-based solution that would provide for accurate delivery of substances for treating dental caries and, in particular, interproximal caries.

To better address one or more of these concerns, a dental medicament applicator is disclosed. In one embodiment of the dental medicament applicator, a placement device is sized for insertion at a dental site, such as an interproximal site. The placement device includes a central body and at least one matrix secured to the central body containing a topical substance, such as a fluoride-containing chemical agent, silver diamine fluoride, or a peptide-based chemical agent, for example. One or more wings extend from the central body to provide subterminal opposition surfaces to hold the placement device during placement. The one or more wings are non-active; that is, free of the topical substance. The active matrix, in response to being physically affixed to the dental site, delivers the topical substance at a controlled rate to the dental site while the placement device dissolves at a quicker controlled rate. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 8A is an illustrative diagram depicting a cross-sectional view of an interproximal space between two teeth where the dental medicament applicator of FIG. 1 is in a first operational configuration;

FIG. 8B is an illustrative diagram depicting a cross-sectional view of an interproximal space between two teeth where the dental medicament applicator of FIG. 8A is in a second operational configuration;

FIG. 8C is an illustrative diagram depicting a cross-sectional view of an interproximal space between two teeth where the dental medicament applicator of FIG. 8A is in a third operational configuration;

FIG. 8D is an illustrative diagram depicting a cross-sectional view of an interproximal space between two teeth where the dental medicament applicator of FIG. 8A is in a fourth operational configuration;

FIG. 8E is an illustrative diagram depicting a cross-sectional view of an interproximal space between two teeth where the dental medicament applicator of FIG. 8A is in a fifth operational configuration;

FIG. 12 is a front elevation view of another embodiment of a dental medicament applicator;

FIG. 13 is a rear elevation view of the dental medicament applicator depicted in FIG. 12;

FIG. 14 is a top plan view of the dental medicament applicator depicted in FIG. 12;

FIG. 15 is a bottom plan view of the dental medicament applicator depicted in FIG. 12;

FIG. 16 is a lateral elevation view of the dental medicament applicator depicted in FIG. 12; and FIG. 17 is another lateral elevation view of the dental medicament applicator depicted in FIG. 12.

DETAILED DESCRIPTION OF THE INVENTION

Figure 3:
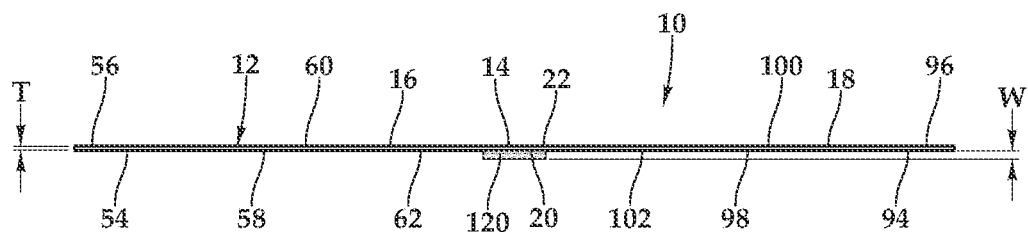
FIG. 3 is a top plan view of the dental medicament applicator depicted in FIG. 1.
Figures 1, 5, 6:
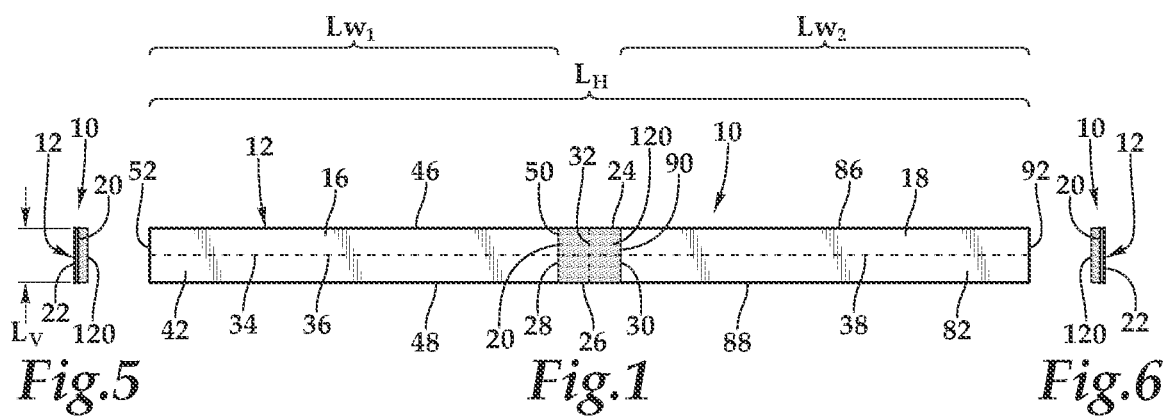
FIG. 1 is a front elevation view of one embodiment of a dental medicament applicator, according to some exemplary aspects of the teachings presented herein.
FIG. 5 is a lateral elevation view of the dental medicament applicator depicted in FIG. 1.
FIG. 6 is another lateral elevation view of the dental medicament applicator depicted in FIG. 1.
Figure 4:
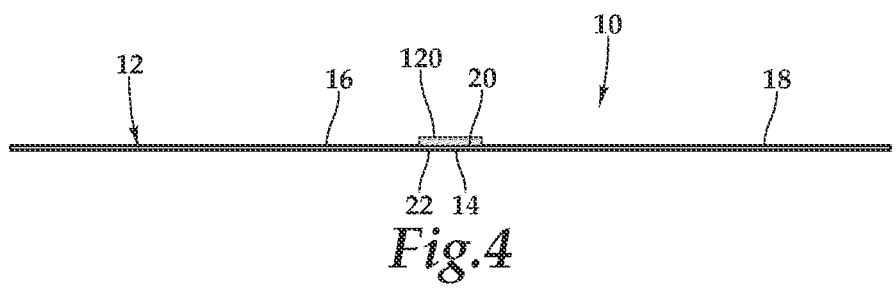
FIG. 4 is a bottom plan view of the dental medicament applicator depicted in FIG. 1.
Figure 2:
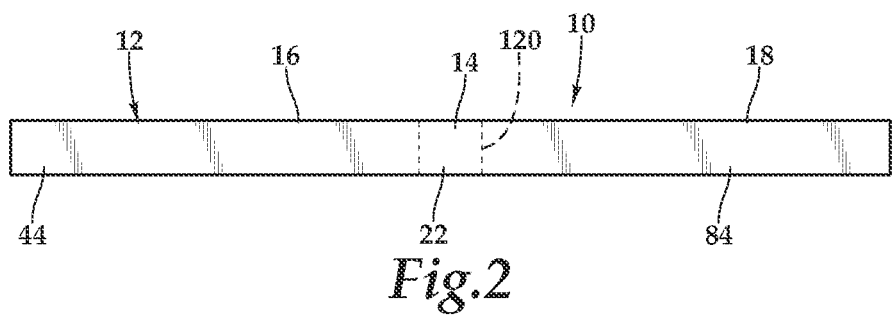
FIG. 2 is a rear elevation view of the dental medicament applicator depicted in FIG. 1.

While the making and using of various embodiments of the present invention are discussed in detail below, it should be appreciated that the present invention provides many applicable inventive concepts, which can be embodied in a wide variety of specific contexts. The specific embodiments discussed herein are merely illustrative of specific ways to make and use the invention, and do not delimit the scope of the present invention.

Referring initially to FIG. 1 through FIG. 6, therein is depicted one embodiment of a dental medicament applicator that may be utilized to treat dental caries and interproximal caries, for example, which is schematically illustrated and designated 10. A placement device 12 is sized for insertion at a dental site, such as an interproximal site. As shown, the placement device 12 includes a central body 14, a wing 16, and a wing 18. The central body 14 may include a front 20, a rear 22, an upper end 24, a lower end 26, a lateral end 28, and a lateral end 30. The placement device 12 also includes a vertical axis 32 and a horizontal axis 34, which includes a transverse axis 36 at the wing 16 and a transverse axis 38 at the wing 18. The vertical axis 32 has a length $L_V$ and the horizontal axis has a length $L_H$. The length $L_V$ may be about 3 mm to about 5 mm in some embodiments. The length $L_H$ may be about 55 mm to about 65 mm. The placement device may also have a thickness T of about 100 microns to about 130 microns.

The wing 16 includes a front 42, a rear 44, an upper end 46, a lower end 48, a proximal end 50, and a distal end 52. The wing 16 has a rectangular form, like a strip, in this embodiment, but it should be appreciated that the wing 16 may have other forms as well. Further, the wing 16 may be at least partially integrated with the central body 14 or the wing 16 may be integral with the central body 14.

As shown in the illustrated embodiment, the wing 16 of the placement device 12 of the dental medicament applicator 10 may include the transverse axis 36 from the distal end 52 of the wing 16 through the proximal end 50 of the wing 16. The transverse axis 36 has a transverse length $L_{W1}$, which is sufficient to provide subterminal opposition surfaces 54, 56, 58, 60 in which palmar surfaces of a thumb and an index finger can hold the wing 16 therebetween. Further, the transverse axis 36 provides a proximal viewing area 62 interposed between the central body 14 and the subterminal opposition surfaces 54, 56, 58, 60. In some embodiments, the transverse length $L_{W1}$ of the transverse axis 36 may be greater than twice the mean width for a human tooth, which may be less than 10 mm. In some embodiments, the transverse length $L_{W1}$ may be greater than 18 mm and in some other embodiments, the transverse length $L_{W1}$ of the transverse axis 36 may be about 25 mm to about 30 mm. The wing 16 may also have a thickness T of about 100 microns to about 130 microns in some embodiments.

The wing 18 may include a structure similar to the structure of the wing 16. More particularly, the wing 18 includes a front 82, a rear 84, an upper end 86, a lower end 88, a proximal end 90, and a distal end 92. The wing 18 has a rectangular form, like a strip, in this embodiment, but it should be appreciated that the wing 18 may have other forms as well. Further, the wing 18 may be at least partially integrated with the central body 14 or the wing 18 may be integral with the central body 14.

As shown in the illustrated embodiment, the wing 18 may include the transverse axis 38 from the distal end 92 of the wing 18 through the proximal end 90 of the wing 18. The transverse axis 38 has a transverse length $L_{W2}$, which is sufficient to provide subterminal opposition surfaces 94, 96, 98, 100 in which palmar surfaces of a thumb and an index finger can hold the wing 18 therebetween. Further, the transverse axis 38 provides a proximal viewing area 102 interposed between the central body 14 and the subterminal opposition surfaces 94, 96, 98, 100. In some embodiments, the transverse length $L_{W2}$ of the transverse axis 38 may be greater than twice the mean width for a human tooth. In some embodiments, the transverse length $L_{W2}$ may be greater than 18 mm and in some other embodiments, the transverse length $L_{W2}$ of the transverse axis 38 may be about 25 mm to about 30 mm. The wing 18 may also have a thickness T of about 100 microns to about 130 microns in some embodiments.

The placement device 12, which, as previously discussed, includes the central body 14 and the wings 16, 18, may include biodegradable materials, bioresorbable materials, or resorbable materials, for example. The placement device 12 may be a polymeric membrane or strip. By way of example and not by way of limitation, the placement device 12 may comprise a synthetic polymer or a natural polymer which may be at least one of polysacaccharides, lipids, polyisoprene, gum and proteins, or any mixture thereof. The natural polymer may be a protein selected from collagen and gelatin, for example. Preferably, the polymer is cross-linked, typically by at least one of glutaraldehyde, formaldehyde, glycol dimethacrylate, tannic acid, and allyl methacrylate. With respect to collagen, by way of example, collagen utilized in the placement device 12 may be untreated or treated with fixing agents to prolong its resistance to digestion. By way of further example, denatured collagen can be impregnated with chromium salts to enhance its tensile strength and retard its absorption. With respect to cross-linking a polymer, a polymeric matrices, such as gelatin matrices, have efficacy when texture is taken into consideration. Gelatin matrices, like collagen, may be lysine-cross linked with glutaraldehyde to address these issues.

Alternatively, the placement device 12 is made of an organic or natural material, such as a macromolecule like acidic proteins, glycoproteins or sulfated polysaccharides, or smaller molecules such as xylitol, polyaspartic acid or polyglutamic acid, for example. More particular examples of natural products include polysaccharide polymers (e.g., pullulan, agar, alginates, carboxymethylcellulose, carrageenan, cellulose, gellan gum, Kelcogel®, Kelcogel® F, Kelco Biopolymers, starches and retted flax extracts), lipids, polyisoprenes (e.g., latex rubber and gutta percha), resins and gums (e.g., tragacanth and storax) and proteins (e.g., alpha or beta chitin, soluble elastin and collagen or denatured collagen in the form of gelatin).

It should be appreciated, however, that a completely natural matrix of gelatin without cross-linking can also be utilized in the placement device 12. Furthermore, natural cross-linkings are also feasible, for example calcium and hydroxylysin or leucine, dihydroxylysine or leucine, lysine, arginine, proteins, polysaccharides such as dextran, lipids such as sodium docusate and dehydrodihydroxylysine or leucine.

Synthetic products may also serve as a composition of the placement device 12 include homopolymers or copolymers with a wide molecular weight range formed by condensation, additional anionic, cationic, and/or catalytic polymerization systems. Examples of such synthetic products for use in the placement device 12 are acrylamide based polymers and a cationic monomer, cyanoacrylates, polycarbonates, polyurethane, polyester urethane dimethacrylate, polycaprolactones, ethyl triglycide methacrylate, polysulphides, povidone, polyacrylic methacrylic acid, acrylic and modifications such as poly(hydroxyethyl methacrylate), poly (methylmethacrylate) modified with small amounts of ethyl, butyl, or other alkyl methacrylates, polyethylene glycol, sodium polyacrylate PEG 400 and PEG 3350, and other carbomers. Some of these are indeed commercial or laboratory products such as polymethylvinylether-co-maleic anhydride and polyvinylether-co-maleic anhydride and polyvinyl pyrrolidone, carboxymethylcellulose, silated hydroxyethylcellulose or hydroxypropyl methylcellulose, hydroxy-propyl methyl cellulose (HPMC, including pharmacy grade HPMC), glycerin, and aqueous methacrylic polymer formulations for sustained and controlled release of dental and other products (e.g., Eudragit® Rohm). These polymers may require activators and cross-linking. However, other agents are at times required, for example retarding agents such as hydroquinone and eugenol. Other yet different examples are zinc eugenolate, petrolateum, and stearyl alcohol. Other gels may be included, such as Carbopol polymers or sodium-based solutions mixed with phosphoric acid and hydrofluoric acid.

The placement device 12 may also include, by way of example, and not by way of limitation, a starch-based polymer selected from the group consisting of native starches, modified starches, and thermoplastic starch polymers. The placement device 12 may also include, by way of further example, and not by way of limitation, at least one synthetic polymer selected from the group consisting of polyvinyl alcohols (PVOHs), polyester amides, polyester urethanes, aliphatic polyesters, aromatic polyesters, and copolymers of aliphatic polyesters and aromatic polyesters.

It is to be appreciated that the degree of cross-linking is of major significance to the rate of release of the active or auxiliary agents, including topical substances, that form a portion of the dental medicament applicator 10. The determination of the degree of cross-linking of the polymeric matrix or matrices in the placement device 12 is informed by the desired application of the dental medicament applicator 10. Examples of factors that may inhibit the biodegradation of the matrix or matrices include are the use of antimicrobial agents, preservatives, sterilizing agent inhibitors, such as inhibitors of matrix metalloptoteinases, and enzyme inhibitors, for example.

The matrices within the placement device 12 may be strengthened not only by cross-linking, but also by other techniques as well. Polymer composite compositions may be utilized in which the polymer fibers, e.g., collagen fibers and gelatin, are strengthened by adding particular catechol-containing compounds, particularly compounds which have two or more catechol groups, to the polymeric material and forming a polymer of the compounds that intercalate within the polymeric material, e.g., forming a polymer composite. The resulting polymer that forms may be a scaffold-like structure throughout the polymeric material without the necessity of cross-linking the individual polymeric materials, e.g., collagen or gelatin polypeptides. This scaffolding provides synthetic polymer fibers having a tensile strength, stiffness, and strain at failure that is comparable to or better than natural polymeric material fibers.

In some embodiments, at least one active matrix 120 is secured to the front 20 of the central body 14 and the at least one active matrix 120 contains a topical substance. The at least one active matrix 120 may have a length and width similar too, including smaller, than the central body 14. With respect to thickness, the active matrix 120 may have a thickness or width W of about 100 microns to about 250 microns or 870 microns in some embodiments. The thickness of the dental medicament applicator 10 in some embodiments is therefore about 200 microns to about 380 microns. In other embodiments, the thickness of the placement device 12 and the active matrix 120 may be adjusted to provide a total thickness of about 500 microns to about 1,000 microns. It should be appreciated that the selection of the topical substance, which will be discussed in further detail hereinbelow, in the active matrix 120 impacts the thickness of the active matrix 120 and therefore the thickness of the placement device 12.

The active matrix 120 may have a composition similar to that of the placement device 12, which may include biodegradable materials, bioresorbable materials, or resorbable materials, for example. By way of example and not by way of limitation, the active matrix 120 may comprise a synthetic polymer or a natural polymer which may be at least one of polysacacchariddes, lipids, polyisoprene, gum and proteins, or any mixture thereof. The natural polymer may be a protein selected from collagen and gelatin, for example. Preferably, the polymer is cross-linked, typically by at least one of glutaraldehyde, formaldehyde, glycol dimethacrylate, tannic acid, and allyl methacrylate. With respect to collagen, by way of example, collagen utilized in the active matrix 120 may be untreated or treated with fixing agents to prolong its resistance to digestion. By way of further example, denatured collagen can be impregnated with chromium salts to enhance its tensile strength and retard its absorption. With respect to cross-linking a polymer, a polymeric matrices, such as gelatin matrices, have efficacy when texture is taken into consideration. Gelatin matrices, like collagen, may be lysine-cross linked with glutaraldehyde to address these issues.

Alternatively, the active matrix 120 is made of an organic or natural material, such as a macromolecule like acidic proteins, glycoproteins or sulfated polysaccharides, or smaller molecules such as xylitol, polyaspartic acid or polyglutamic acid, for example. More particular examples of natural products include polysaccharide polymers (e.g., pullulan, agar, alginates, carboxymethylcellulose, carrageenan, cellulose, gellan gum, Kelcogel®, Kelcogel® F, Kelco Biopolymers, starches and retted flax extracts), lipids, polyisoprenes (e.g., latex rubber and gutta percha), resins and gums (e.g., tragacanth and storax) and proteins (e.g., alpha or beta chitin, soluble elastin and collagen or denatured collagen in the form of gelatin).

It should be appreciated, however, that a completely natural matrix of gelatin without cross-linking can also be utilized in the active matrix 120. Furthermore, natural cross-linkings are also feasible, for example, calcium and hydroxylysin or leucine, dihydroxylysine or leucine, lysine, arginine, proteins, polysaccharides such as dextran, lipids such as sodium docusate, and dehydrodihydroxylysine or leucine.

Synthetic products may also serve as a composition of the active matrix 120 include homopolymers or copolymers with a wide molecular weight range formed by condensation, additional anionic, cationic, and/or catalytic polymerization systems. Examples of such synthetic products for use in the placement device 12 are acrylamide based polymers and a cationic monomer, cyanoacrylates, polycarbonates, polyurethane, polyester urethane dimethacrylate, polycaprolactones, ethyl triglycide methacrylate, polysulphides, povidone, polyacrylic methacrylic acid, acrylic and modifications such as poly(hydroxyethyl methacrylate), poly (methylmethacrylate) modified with small amounts of ethyl, butyl, or other alkyl methacrylates, polyethylene glycol, sodium polyacrylate PEG 400 and PEG 3350, and other carbomers. Some of these are indeed commercial or laboratory products, such as polymethylvinylether-co-maleic anhydride, polyvinylether-co-maleic anhydride, and polyvinyl pyrrolidone, carboxymethylcellulose, silated hydroxyethylcellulose or hydroxypropyl methylcellulose, hydroxypropyl methyl cellulose (HPMC, including pharmacy grade HPMC), glycerin, and aqueous methacrylic polymer formulations for sustained and controlled release of dental and other products (e.g., Eudragit® Rohm). These polymers may require activators and cross-linking. However, other agents are at times required, for example, retarding agents such as hydroquinone and eugenol. Other yet different examples are zinc eugenolate, petrolateum, and stearyl alcohol. Other gels may be included such as Carbopol polymers or sodium-based solutions mixed with phosphoric acid and hydrofluoric acid.

The active matrix 120 may also include, by way of example, and not by way of limitation, a starch-based polymer selected from the group consisting of native starches, modified starches, and thermoplastic starch polymers. The active matrix 120 may also include, by way of further example, and not by way of limitation, at least one synthetic polymer selected from the group consisting of polyvinyl alcohols (PVOHs), polyester amides, polyester urethanes, aliphatic polyesters, aromatic polyesters, and copolymers of aliphatic polyesters and aromatic polyesters.

It is to be appreciated that the degree of cross-linking is of major significance to the rate of release of the active or auxiliary agents, including topical substances, that form the active matrix 120. The determination of the degree of cross-linking of the polymeric matrix or matrices in the active matrix 120 is informed by the desired application of the dental medicament applicator 10. Examples of factors that may inhibit the biodegradation of the matrix or matrices include the use of antimicrobial agents, preservatives, sterilizing agent inhibitors, such as inhibitors of matrix metalloptoteinases, and enzyme inhibitors, for example.

The matrices within the active matrix 120 may be strengthened not only by cross-linking, but also by other techniques as well. Polymer composite compositions may be utilized in which the polymer fibers, e.g., collagen fibers and gelatin, are strengthened by adding particular catechol-containing compounds, particularly compounds which have two or more catechol groups, to the polymeric material and forming a polymer of the compounds that intercalate within the polymeric material, e.g., forming a polymer composite. The resulting polymer that forms may be a scaffold-like structure throughout the polymeric material without the necessity of cross-linking the individual polymeric materials, e.g., collagen or gelatin polypeptides. This scaffolding provides synthetic polymer fibers having a tensile strength, stiffness, and strain at failure that is comparable to or better than natural polymeric material fibers.

The active matrix 120, in response to being physically affixed to the dental site, delivers the topical substance at a controlled rate to the dental site. The topical substance may be a fluoride-containing chemical agent. By way of example, and not by way of limitation, the topical substance within the active matrix 120 may be any one of inorganic or organic fluoride-containing chemical agents, including sodium fluoride, stannous fluoride, stannous hexafluorozirconate, calcium fluoride, difluorosilane, hydrogen fluoride, sodium monofluorophosphate, ytterbium trifluoride, sodium hexafluorosilicate, ammonium fluoride, amine fluoride, and fluoroaluminosilicate glass, as well as any mixture thereof. The period of fluoridation required by the chemical agent is dependent on the type of fluoride, concentration, and period of delivery. It should be appreciated that other chemical or physical interventions and the type of surface or lesion being treated may also impact the period of fluoridation. Further, chronic toxicity due to fluoride (F) may be reached at 0.1 mg F/Kg of body weight. Thus, the weight of the patient impacts fluoride concentration as well. By way of example, and not by way of limitation, in applications where sodium fluoride is selected, the applicable concentration will be 1%-4%. By way of further example, and not by way of limitation, the sodium fluoride will have a concentration of about 1% to 9% or, in further examples, the concentration may be 3% to 7%.

That is, with respect to fluoride, the active matrix 120 may have a topical substance having about 0.2 mg to about 1.5 mg of fluoride with some embodiments having about 0.2 mg to about 0.3 mg. It should be appreciated that the amount of fluoride may vary and, in general, a lower amount of fluoride in the topical substance will translate into a thinner active matrix and make placement easier in tight interproximal spaces.

In another implementation, the topical substance may be silver diamine fluoride. Silver diamine fluoride (SDF), a clear liquid that combines the antibacterial effects of silver and the remineralizing effects of fluoride, is a promising therapeutic agent for managing caries lesions in young children and those with special care needs. SDF has only recently become available in the United States. SDF may also have the name "silver-diamine fluoride" or "silver hydrazine fluoride." SDF is frequently utilized as an aqueous SDF, 34% to 42% weight/volume, with 38% weight volume being preferred in many cases, with a presentation as a light-sensitive liquid with ammonia odor and blue coloring having a specific gravity of about 1.25. When the silver in SDF is applied to a dental site on a tooth, it oxidizes and leaves a black stain on the damaged cavity portion of the tooth and may cause staining in other areas of the oral cavity. Therefore, SDF must be delivered at a controlled rate to the desired dental site. The dental medicament applicator 10 accomplishes this goal as will be discussed in further detail hereinbelow.

As mentioned, the body 14, in response to being physically affixed to the dental site, delivers the topical substance at a controlled rate to the dental site. The topical substance may be a peptide-based chemical agent. The peptide-based chemical agent may include, by way of example and not by way of limitation, polypeptides, or the composition may further comprise one or more other active agents suitable for an intended use, including but not limited to antimicrobial polypeptides (inhibiting bacterial infection), biomineralization-promoting polypeptides (i.e., any polypeptides that are useful for controlling or promoting biomineralization), inorganic material-binding polypeptides, three-dimensional scaffold-forming polypeptides, collagen, chitosan, amphiphilic peptides, protein-binding polypeptides, enamelin-derived polypeptides, tuftelin-derived peptides, statherin-derived polypeptides, dentin-derived polypeptides, bone sialoprotein-derived polypeptides, osteocalcin-derived polypeptides, osteopontin-derived polypeptides, proteins with caries inhibitory activity, casein, and bone morphogenetic-derived polypeptides.

By way of further example, and not by way of limitation, the topical substance, when including the peptide-based chemical agent, may be a combination of amelogenin, an inorganic or organic fluoride-containing chemical agent, an inorganic or organic calcium-containing chemical agent, and an inorganic or organic phosphate-containing chemical agent. By way of further example, and not by way of limitation, the topical substance may be at least one of amelogenin, an inorganic or organic fluoride-containing chemical agent, an inorganic or organic calcium-containing chemical agent, and an inorganic or organic phosphate-containing chemical agent.

Amelogenins are a group of protein isoforms produced by alternative splicing or proteolysis from the AMELX gene, on the X chromosome, and also the AMELY gene in males, on the Y chromosome. Amelogenins are involved in amelogenesis, the development of enamel. Amelogenins are type of extracellular matrix protein, which, together with ameloblastins, enamelins and tuftelins, direct the mineralization of enamel to form a highly organized matrix of rods, interrod crystal and proteins. As previously discussed, the inorganic or organic fluoride-containing chemical agent may be sodium fluoride, Stannous fluoride, Stannous hexafluorozirconate, calcium fluoride, difluorosilane, hydrogen fluoride, sodium monofluorophosphate, ytterbium trifluoride, sodium hexafluorosilicate, ammonium fluoride, amine fluoride, and fluoroaluminosilicate glass, as well as any mixture thereof.

By way of example, and not by way of limitation, the inorganic or organic calcium-containing chemical agent may be integrated into calcium phosphates, casein phosphopeptide/amorphous calcium phosphate nanocomplexes, casein phosphopeptide-amorphous calcium phosphate, octacalcium phosphate complexes, calcium phosphate crystal structures, dicalcium phosphate dihydrate-based compounds, calcium phosphate pastes, or in vitro calcium phosphate mineralizable compounds. Also, by way of example and not by way of limitation, the inorganic or organic phosphate-containing chemical agent may be integrated into calcium phosphates, casein phosphopeptide/amorphous calcium phosphate nanocomplexes, casein phosphopeptide-amorphous calcium phosphate, octacalcium phosphate complexes, calcium phosphate crystal structures, dicalcium phosphate dihydrate-based compounds, calcium phosphate pastes, or in vitro calcium phosphate mineralizable compounds.

As outlined hereinabove, the dental medicament applicator 10 consists of the placement device 12 including the central body 14 having the wings 16, 18. The active matrix 120 having the topical substance is connected to the central body 14. Further, as discussed above, the placement device 12 and the active matrix 120 may be manufactured using a number of techniques appropriate to water-soluble polymers (synthetic, semi-synthetic, or natural) or polysaccharides including, but not limited to, as discussed above, polyethylene glycol, polyacrylamides, polyacrylic acid copolymer, polyvinyl alcohol, xanthan gum, pectines, chitosan derivatives, dextran, carrageenan, guar gum, hydroxy propyl cellulose, hydroxy ethyl cellulose, sodium carboxy methyl cellulose, and hyaluronic acid. Also, as previously discussed, with respect to polysaccharide polymers, pullulan, agar, alginates, carboxymethylcellulose, carrageenan, cellulose, gellan gum, Kelcogel®, Kelcogel® F, Kelco Biopolymers, starches and retted flax extracts are also suitable. Other examples of natural products that are suitable include lipids, polyisoprenes (e.g., latex rubber and gutta percha), resins and gums (e.g., tragacanth and storax) and proteins (e.g., alpha or beta chitin, soluble elastin, and collagen or denatured collagen in the form of gelatin).

Any method of sealing the water-soluble films, i.e., the active matrix 120 to the central body 14, may be used during manufacturing. Such manufacturing methods include the use of an adhesive or heat sealing. Other methods include infra-red, radio frequency, ultrasonic, laser, solvent, and vibration and spin welding sealing. The seal desirably is water-soluble. A suitable heat-sealing temperature is, for example, 120° C. to 195° C., especially 140° C. to 150° C. A suitable sealing pressure is, for example, from 250 kPa to 600 kPa, especially 276 kPa to 552 kPa, more especially from 345 kPa to 483 kPa or from 400 kPa to 800 kPa, especially 500 kPa to 700 kPa, for example depending on the heat-sealing machine used. Suitable sealing dwell times are 0.4 to 2.5 seconds.

Using these techniques, the active matrix 120 is bonded to the central body 14 of the placement device 12 by simply applying water to the back of the active matrix 120 and then using pressure to adhere the active matrix to the central body 14. Depending upon the desired composition of the active matrix 120, an adhesive can also be substituted in lieu of water to moisten the active matrix 120 and then apply pressure to seal the active matrix to the central body 14.

Figure 7:
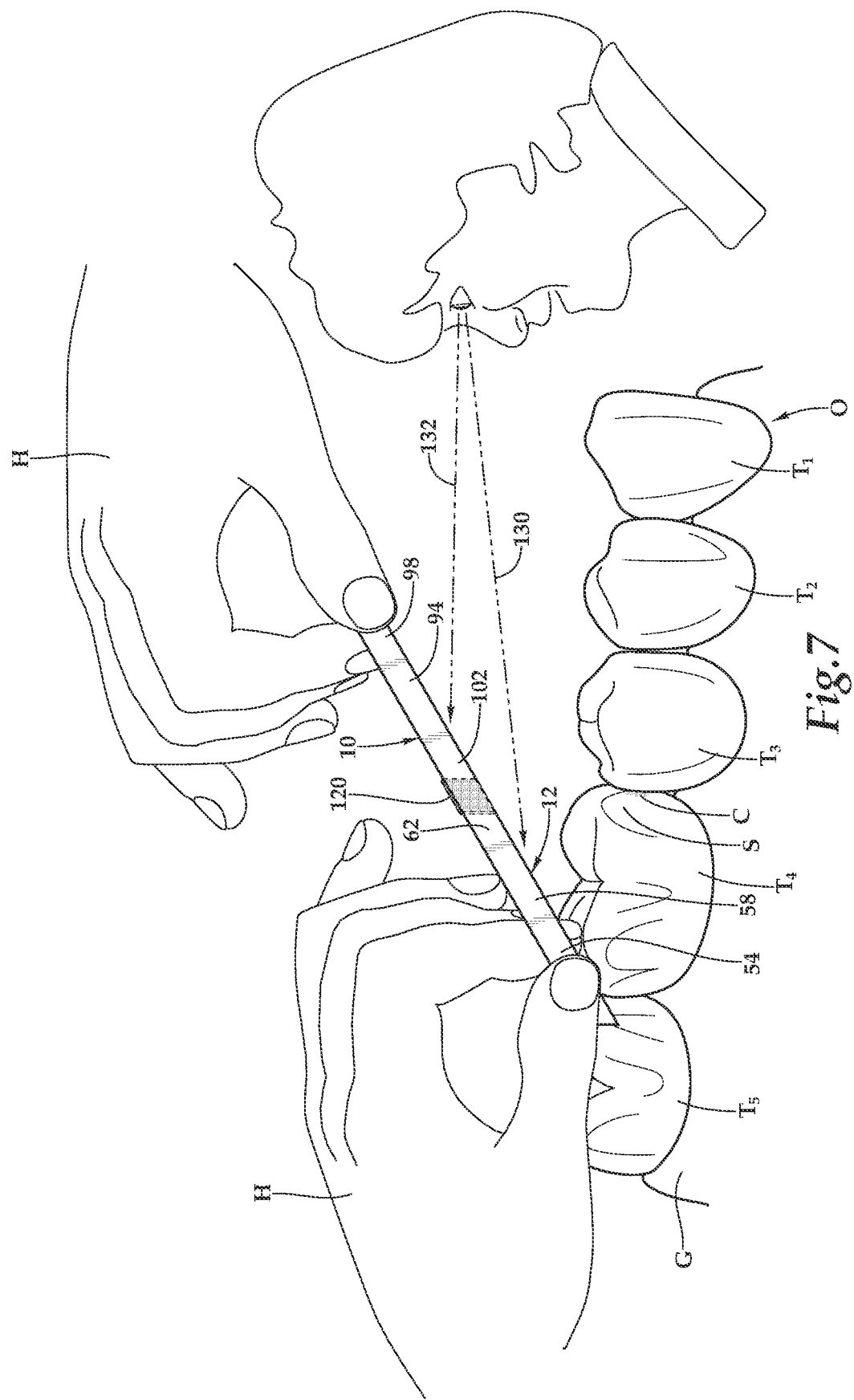
FIG. 7 is an illustrative diagram depicting a lingual view from a tongue of an oral cavity where the dental medicament applicator of FIG. 1 is being utilized, according to some exemplary aspects of the teachings presented herein.

Referring now to FIG. 7 through FIG. 8E, in one operational embodiment, the dental medicament applicator 10 is being utilized within an oral cavity O having teeth $T_1$, $T_2$, $T_3$, $T_4$, $T_5$, $T_6$, $T_7$, $T_8$, $T_9$, and $T_{10}$ as well as gum tissue G. Dental caries C, which represent the dental site, are located on an interproximal surface S of tooth $T_4$. A dental professional having hands H is positioning the dental medicament applicator 10 with the use of the wings 16, 18 in a direction of placement A between teeth $T_3$ and $T_4$. Prior to the dental professional placing the dental medicament applicator 10, various preparatory steps may have been taken. By way of example and not by way of limitation, an approach using dental separators to open the interproximal contact to allow the dental professional to more easily place the dental medicament applicator 10 may be utilized.

As best seen in FIG. 8A and FIG. 8B, the dental professional positions the placement device 12 of the dental medicament applicator 10 over the dental caries C, such that the active matrix 120 will contact the dental caries C. As shown, the proximal viewing areas 62, 102 provide line-of-sight corridors 130, 132 that are utilized to correctly position the central body 14 of the dental medicament applicator 10 such that the wings 16, 18 are adjacent to the dental caries C and in position to contact adjacent or proximate dental surfaces. The subterminal opposition surfaces 54, 56, 58, 60 provide multiple contact points for the dental professional or other user to position the dental medicament applicator— whether using hands or self-locking tweezers, for example—while the dental professional or other user utilizes the line-of-sight corridors 130, 132 for visual confirmation of correct placement. As also shown, the wings 16, 18 may have a different and greater transparency than the central body 14 to create visual distinction therebetween. Such visual distinction further assists in placement and demarcates the wings 16, 18 which have an absence of the topical substance from the active matrix 120, which includes the topical substance therein. Further, to assist with placement, the wings 16, 18 have a larger surface area than the active matrix 120 to provide sufficient space for maneuvering the dental medicament applicator 10 within the mouth, including avoiding unwanted contact with the check and tongue. Additionally, the wings 16, 18 are sculptable and may each be appropriately cut to optimize placement.

As best seen in FIG. 8B and FIG. 8C, once the body 14 of the dental medicament applicator 10 is correctly positioned and affixed to the dental site, the dental professional selectively contacts the wings 14, 16 to contact adjacent or proximate dental surfaces. As best seen in FIG. 8C, FIG. 8D, the placement device 14, in response to being physically affixed at the dental site, dissolves at a controlled rate, while the active matrix 120 delivers the topical substance at a controlled rate to the dental caries C during a slower dissolving which involves a gelatinous stage. The active matrix 120 is then bio-reabsorbed leaving a treated dental carie CT, which is best seen in FIG. 8E. In this manner the dental medicament applicator 10 provides simplified and accelerated treatment of interproximal caries that is targeted to a specific dental site, thereby mitigating the risk of undesired contact between the topical substance and other bone or tissue.

The dental medicament applicator 10 provides resorbable, water-based polymers that can be impregnated with fluoride or other materials such as silver diamine fluoride (SDF) or amelogenin peptides, and bonded together, along with multiple other possible polymer compounds and ratios that produce varied times of release of the fluoride and that also allow better adherence and longer presence of the medicated active matrix to the tooth. These resorbable, water-based polymers also have handling properties for the clinician that avoid crumbling upon insertion.

The dental medicament applicator 10 may be placed by either a dental professional or a consumer into the affected interproximal space by simply removing a fresh dental medicament applicator 10 from a sealed pouch, grasping the wings 16, 18 between each thumb and forefinger, gently pulling the placement device 12 taut and sliding the placement device 12 with the active matrix 120 facing the dental caries into the interproximal space. The dental professional or consumer will center the active matrix 120 over the incipient lesion and then bend the wings 16, 18 around the interproximal areas comprising mesial and/or distal tooth surfaces. Once released, saliva from the mouth or a couple of drops of water from an air/water syringe onto the wings 16, 18 will start the dissolution and/or resorptive process. The wings 16, 18 may be completely dissolve in about 20 to about 60 seconds, during which time the active matrix 120, which may be fluoride-impregnated, will begin to become gelatinous and begin to release sodium fluoride into the area with the lesion. In some embodiments, the active matrix 120 will release fluoride for about 30 to about 90 minutes after which the matrix will completely dissolve.

Patients may then be evaluated for risk level which will determine frequency of treatment. If a patient has two or more incipient lesions, then such a patient may be considered high risk by dental guidelines. High risk patients may require reapplication every three months until the dental professional confirms that the lesions have been arrested. If the patient is determined to be normal risk, the dental medicament applicator 10 should be reapplied every six months during routine check-ups. The patient requires no monitoring and is free to go once the procedure has been accomplished.

Figure 9:
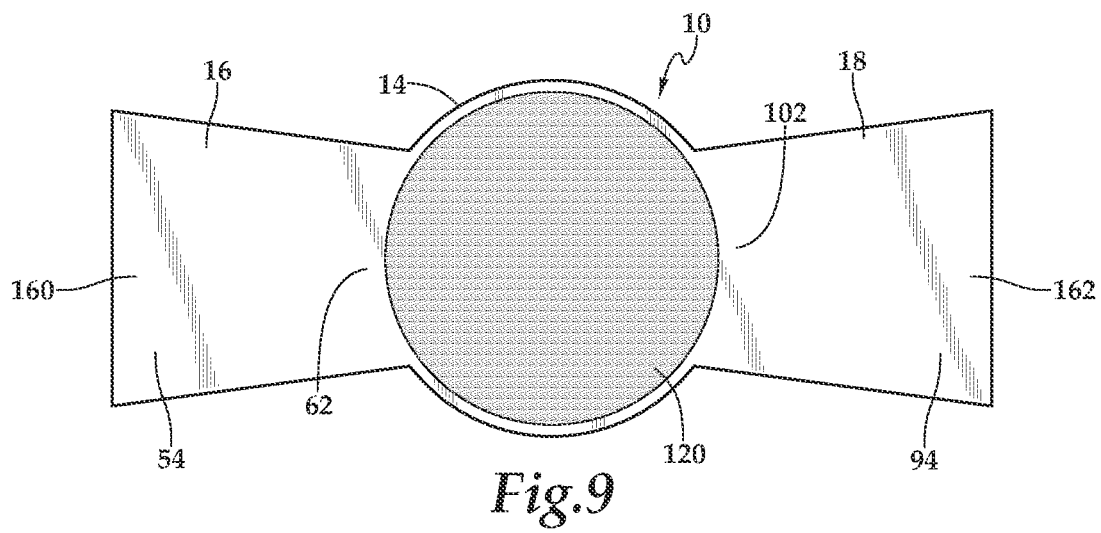
FIG. 9 is a front elevation view of a further embodiment of a dental medicament applicator.

Other embodiments of the dental medicament applicator 10 will now be presented in FIG. 9 through FIG. 17. Referring initially to FIG. 9, the dental medicament applicator 10 includes the central body 14 with the wings 16, 18, as well as the active matrix 120. The wing 16 has a polygon form 160, which is shown as an isosceles trapezium. Similarly, the wing 18 has a polygon form 162, which is also shown as an isosceles trapezium. The embodiment of FIG. 9 and the following embodiments in FIGS. 10-17 all show the dental medicament applicator 10 having the wings 16, 18 with both subterminal opposition surfaces, such as the subterminal opposition surfaces 54, 94 in FIG. 9 through FIG. 11, and proximal viewing areas, such as the proximal viewing areas 62, 102 in FIG. 9 through FIG. 11. Each of these embodiments shows one of the many varied forms of the dental medicament application 10 that fall within the teachings presented herein.

Figure 10:
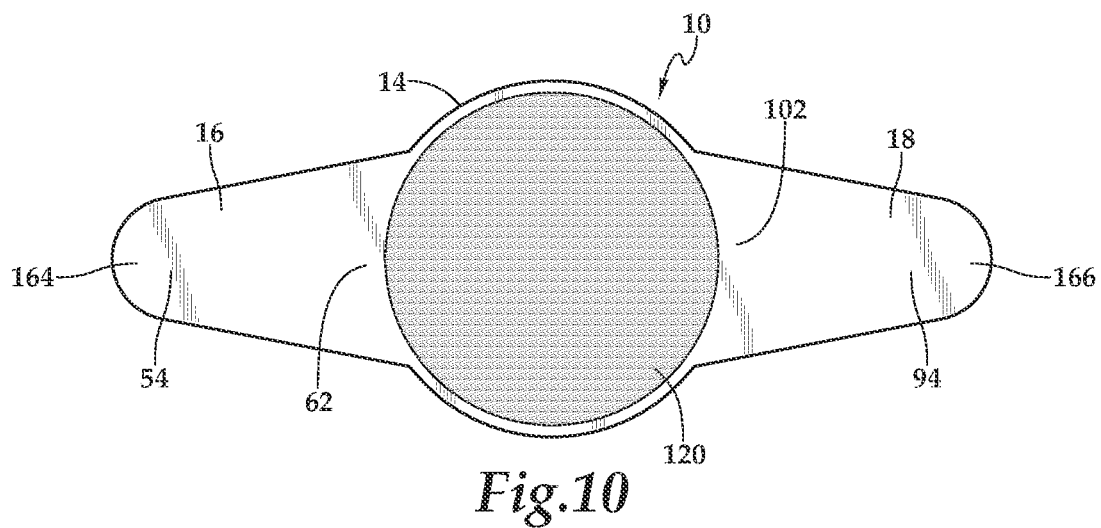
FIG. 10 is a front elevation view of a still further embodiment of a dental medicament applicator.
Figure 11:
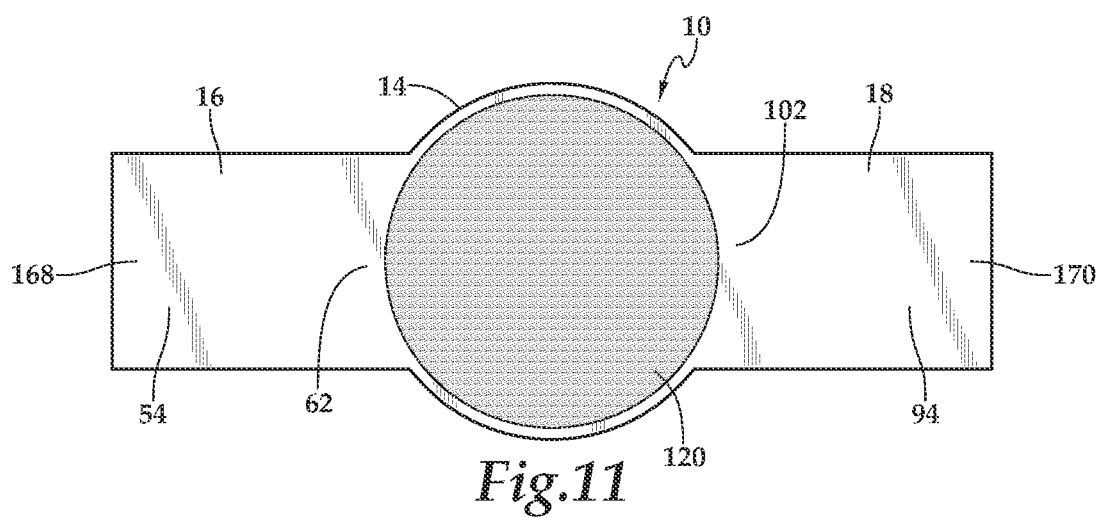
FIG. 11 is a front elevation view of an additional embodiment of a dental medicament applicator.

Referring now to FIG. 10, the dental medicament applicator 10 includes the central body 14 with the wings 16, 18, as well as the active matrix 120. The wing 16 has a semi-elliptical form 164. Similarly, the wing 18 has a semi-elliptical form 166. Referring now to FIG. 11, the dental medicament applicator 10 includes the central body 14 with the wings 16, 18, as well as the active matrix 120. The wing 16 has a rectangular form 168. Similarly, the wing 18 has a rectangular form 170.

Referring now to FIG. 12 through FIG. 17, in some embodiments of the dental medicament applicator 10, a placement device 182 is sized for insertion at a dental site, such as an interproximal site. As shown, the placement device 182 includes a central body 184 having a front 186, a rear 188, an upper end 190, a lower end 192, a lateral end 194, and a lateral end 196. The body 184 also includes a vertical axis 198 and a horizontal axis 200. A wing 210 includes a front 212, a rear 214, an upper end 216, a lower end 218, a proximal end 230, and a distal end 232. The wing 210 has the shape of a lobe 234 and includes subterminal opposition surfaces 236 and a proximal viewing area 238. It should be appreciated that the embodiments of the dental medicament applicator 10 presented in FIG. 9 through FIG. 17 are exemplary and intended to show variations in the design of the dental medicament applicator 10.

Relative terms, such as, but not limited to, "upper," "lower," "front," "rear," "lateral," "vertical," or "horizontal" have been used herein to describe one element's relationship to another element as illustrated in the figures. Such relative terms are intended to encompass different orientations of the device in addition to the orientation depicted in the figures and the use of such relative terms should not be construed as limiting. Further, the order of execution or performance of the methods and techniques illustrated and described herein is not essential, unless otherwise specified. That is, elements of the methods and techniques may be performed in any order, unless otherwise specified, and that the methods may include more or less elements than those disclosed herein. For example, it is contemplated that executing or performing a particular element before, contemporaneously with, or after another element are all possible sequences of execution.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A dental medicament applicator comprising:
   a placement device sized for insertion at a dental site, the dental site including an interproximal site with a dental caries, the placement device comprised of hydroxypropyl methyl cellulose (HPMC) polymers, the placement device including a central body, a first wing, and a second wing;
   the first wing providing subterminal opposition surfaces in which palmar surfaces of a thumb and an index finger can hold the first wing therebetween, the first wing being sized to bend around the interproximal site so that, when bent, the first wing engages a dental surface adjacent the dental site and stabilizes the central body over the dental caries, the first wing being free of a topical substance for treating incipient lesions;

the second wing providing subterminal opposition surfaces in which palmar surfaces of a thumb and an index finger can hold the second wing therebetween, the second wing being sized to bend around the interproximal site so that, when bent, the second wing engages a dental surface adjacent the dental site and stabilizes the central body over the dental caries, the second wing being free of the topical substance;

at least one active matrix secured to the front of the central body, the at least one active matrix comprised of pullulan polymers containing the topical substance;

each of the first wing and the second wing having a larger surface area than the at least one active matrix;

the placement device, in response to being physically affixed to the dental site and bent around the interproximal site and the adjacent dental surfaces, dissolving at a first controlled rate; and the at least one active matrix, in response to the central body being physically affixed over the dental caries, transitioning to a gelatinous state while delivering the topical substance to the dental caries at a second controlled rate that is slower than the first controlled rate, the gelatinous active matrix thereafter dissolving and being bio-reabsorbed, whereby the dental medicament applicator completely dissolves following dissolution of the placement device at the first controlled rate and delivery of the topical substance at the second controlled rate.

2. The dental medicament applicator as recited in claim 1, wherein the central body and the first wing are at least partially integrated.

3. The dental medicament applicator as recited in claim 1, wherein the central body and the first wing are integral.

4. The dental medicament applicator as recited in claim 1, wherein the central body and the second wing are at least partially integrated.

5. The dental medicament applicator as recited in claim 1, wherein the central body and the second wing are integral.

6. The dental medicament applicator as recited in claim 1, wherein the central body and the at least one active matrix are at least partially integrated.

7. The dental medicament applicator as recited in claim 1, wherein the central body and the at least one active matrix are integral.

8. The dental medicament applicator as recited in claim 1, wherein the first wing further comprises a proximal viewing area interposed between the central body and the subterminal opposition surfaces.

9. The dental medicament applicator as recited in claim 1, wherein the second wing further comprises a proximal viewing area interposed between the central body and the subterminal opposition surfaces.

10. The dental medicament applicator as recited in claim 1, wherein each of the first and second wings have a first transparency and the at least one active matrix has a second transparency, the first transparency being visually different than the second transparency.

11. The dental medicament applicator as recited in claim 1, wherein each of the first and second wings have a first transparency and the at least one active matrix has a second transparency, the first transparency being more transparent than the second transparency.

12. The dental medicament applicator as recited in claim 1, wherein each of the first and second wings comprise a shape selected from the group consisting of single lobes, double lobes, polygon forms, and rectangular forms.

13. The dental medicament applicator as recited in claim 1, wherein the placement device further comprises a material selected from the group consisting of biodegradable materials, bioresorbable materials, and resorbable materials.

14. The dental medicament applicator as recited in claim 1, wherein the at least one matrix further comprises a material selected from the group consisting of biodegradable materials, bioresorbable materials, and resorbable materials.

15. The dental medicament applicator as recited in claim 1, wherein the topical substance further comprises at least one of a fluoride-containing chemical agent and a calcium-containing chemical agent.

16. The dental medicament applicator as recited in claim 1, wherein the topical substance further comprises silver diamine fluoride.

17. The dental medicament applicator as recited in claim 1, wherein the topical substance further comprises a peptide-based chemical agent.

18. The dental medicament applicator as recited in claim 1, wherein the topical substance further comprises a peptide-based chemical agent, the peptide-based chemical agent including a combination of amelogenin, a fluoride-containing chemical agent, a calcium-containing chemical agent, and a phosphate-containing chemical agent.

19. A dental medicament applicator comprising:

a placement device sized for insertion at a dental site, the dental site including an interproximal site with a dental caries, the placement device comprised of hydroxypropyl methyl cellulose (HPMC) polymers, the placement device including a central body, a first wing, and a second wing;

the first wing providing subterminal opposition surfaces in which palmar surfaces of a thumb and an index finger can hold the first wing therebetween, the first wing being sized to bend around the interproximal site so that, when bent, the first wing engages a dental surface adjacent the dental site and stabilizes the central body over the dental caries, the first wing being free of a topical substance for treating incipient lesions;

the second wing providing subterminal opposition surfaces in which palmar surfaces of a thumb and an index finger can hold the second wing therebetween, the second wing being sized to bend around the interproximal site so that, when bent, the second wing engages a dental surface adjacent the dental site and stabilizes the central body over the dental caries, the second wing being free of the topical substance;

at least one active matrix secured to the front of the central body, the at least one active matrix comprised of pullulan polymers containing the topical substance;

each of the first wing and the second wing having a larger surface area than the at least one active matrix;

the placement device, in response to being physically affixed to the dental site and bent around the interproximal site and the adjacent dental surfaces, dissolving at a first controlled rate within about 20 seconds to about 60 seconds; and the at least one active matrix, in response to the central body being physically affixed over the dental caries, transitioning to a gelatinous state while delivering the topical substance to the dental caries at a second controlled rate within about 30 minutes to about 90 minutes, the gelatinous active matrix thereafter dissolving and being bio-reabsorbed, whereby the dental medicament applicator completely dissolves following dissolution of the placement device at the first controlled rate and delivery of the topical substance at the second controlled rate.

20. A dental medicament applicator comprising:

a placement device sized for insertion at a dental site, the dental site including an interproximal site with a dental caries, the placement device comprised of water-soluble polysaccharide polymers, the placement device including a central body, a first wing, and a second wing;

the first wing providing subterminal opposition surfaces in which palmar surfaces of a thumb and an index finger can hold the first wing therebetween, the first wing being sized to bend around the interproximal site so that, when bent, the first wing engages a dental surface adjacent the dental site and stabilizes the central body over the dental caries, the first wing being free of a topical substance for treating incipient lesions;

the second wing providing subterminal opposition surfaces in which palmar surfaces of a thumb and an index finger can hold the second wing therebetween, the second wing being sized to bend around the interproximal site so that, when bent, the second wing engages a dental surface adjacent the dental site and stabilizes the central body over the dental caries, the second wing being free of a topical substance for treating incipient lesions;

at least one active matrix secured to the front of the central body, the at least one active matrix comprised of water-soluble polysaccharide polymers containing the topical substance;

the placement device, in response to being physically affixed to the dental site and bent around the interproximal site and the adjacent dental surfaces, dissolving at a first controlled rate; and the at least one active matrix, in response to the central body being physically affixed over the dental caries, transitioning to a gelatinous state while delivering the topical substance to the dental caries at a second controlled rate that is slower than the first controlled rate, the gelatinous active matrix thereafter dissolving and being bio-reabsorbed, whereby the dental medicament applicator completely dissolves following dissolution of the placement device at the first controlled rate and delivery of the topical substance at the second controlled rate.

21. The dental medicament applicator of claim 20, wherein the dental surface adjacent the dental site is a mesial or distal surface of the same tooth that contains the dental caries, the first wing and the second wing being configured, when bent, to engage that mesial or distal surface to stabilize the central body.

22. The dental medicament applicator of claim 20, wherein the dental surface adjacent the dental site is a mesial or distal surface of a tooth immediately adjacent to the tooth that contains the dental caries, the first wing and the second wing being configured, when bent, to engage that adjacent-tooth surface to stabilize the central body.

23. The dental medicament applicator of claim 1, wherein the dental surface adjacent the dental site is a mesial or distal surface of the same tooth that contains the dental caries, the first wing and the second wing being configured, when bent, to engage that mesial or distal surface to stabilize the central body.

24. The dental medicament applicator of claim 1, wherein the dental surface adjacent the dental site is a mesial or distal surface of a tooth immediately adjacent to the tooth that contains the dental caries, the first wing and the second wing being configured, when bent, to engage that adjacent-tooth surface to stabilize the central body.

* * * * *